United States Patent
Jeong et al.

(10) Patent No.: US 9,846,113 B2
(45) Date of Patent: Dec. 19, 2017

(54) INTERFACIAL ADHESION STRENGTH MEASURING APPARATUS AND METHOD OF A GAS DIFFUSION LAYER FOR FUEL CELLS

(71) Applicants: Hyundai Motor Company, Seoul (KR); Korea Advanced Institute of Science and Technology, Daejeon (KR)

(72) Inventors: Byeong Heon Jeong, Gyeonggi-Do (KR); Bo Ki Hong, Seoul (KR); Taek Soo Kim, Daejeon (KR); Sanwi Kim, Gyeonggi-Do (KR)

(73) Assignees: Hyundai Motor Company, Seoul (KR); Korea Advanced Institute of Science and Technology, Daejeon (KR)

( * ) Notice: Subject to any disclaimer, the term of this patent is extended or adjusted under 35 U.S.C. 154(b) by 105 days.

(21) Appl. No.: 14/483,432

(22) Filed: Sep. 11, 2014

(65) Prior Publication Data
US 2015/0276579 A1 Oct. 1, 2015

(30) Foreign Application Priority Data
Apr. 1, 2014 (KR) .................. 10-2014-0038880

(51) Int. Cl.
*G01N 19/04* (2006.01)
*G01N 19/00* (2006.01)

(52) U.S. Cl.
CPC ..... *G01N 19/04* (2013.01); *G01N 2203/0091* (2013.01)

(58) Field of Classification Search
CPC .............. G01N 2203/0091; G01N 19/04
See application file for complete search history.

(56) References Cited

U.S. PATENT DOCUMENTS 5,438,863 A * 8/1995 Johnson ............... G01N 3/08
                                                   73/150 A
6,553,843 B1 * 4/2003 Courtade ............. G01N 3/04
                                                   73/827
(Continued)

FOREIGN PATENT DOCUMENTS

JP    2004-214045 A    7/2004
JP    2008-053084 A    3/2008
(Continued)

OTHER PUBLICATIONS

Title "Hysol EA 956". Pertinent p. 1. Date accessed: May 15, 2016. URL: https://tds.us.henkel.com/NA/UT/HNAUTTDS.nsf/web/6593E86B27A94FAB8525715C001BD45B/$File/Hysol_EA_956-EN.pdf.*

*Primary Examiner* — Daniel J Colilla
*Assistant Examiner* — Ruben Parco, Jr.
(74) *Attorney, Agent, or Firm* — Mintz Levin Cohn Ferris Glovsky and Popeo, P.C.; Peter F. Corless

(57) ABSTRACT

An interfacial adhesion strength measuring apparatus of a gas diffusion layer for a fuel cell is provided. The apparatus includes a pair of load applying parts that are each adhered to outer surfaces of a substrate configuring the gas diffusion layer of the fuel cell and a micro porous layer coated on the substrate and is configured to apply a tension force in a direction in which the substrate and the micro porous layer are separated from each other. A first adhering part is applied to one of the load applying parts and is adhered to the substrate and a second adhering part is applied to the other of the load applying parts and is adhered to the micro porous layer. In addition, the first and second adhering parts contain materials of which contact angles with the substrate or the micro porous layer are different from each other, respectively.

12 Claims, 4 Drawing Sheets

(56) References Cited

U.S. PATENT DOCUMENTS

| | | | |
|---|---|---|---|
| 7,628,066 B2 | 12/2009 | Deng et al. | |
| 2005/0193829 A1* | 9/2005 | Brinz | G01N 3/08 73/794 |
| 2011/0239774 A1* | 10/2011 | Schuyler | G01N 3/32 73/812 |

FOREIGN PATENT DOCUMENTS

| | | |
|---|---|---|
| JP | 2008-146984 A | 6/2008 |
| KR | 10-0902316 | 6/2009 |
| KR | 10-2010-0004495 | 1/2010 |
| KR | 10-2010-0102358 | 9/2010 |
| KR | 10-2013-0103049 | 9/2013 |
| KR | 10-1335686 | 12/2013 |

* cited by examiner

INTERFACIAL ADHESION STRENGTH MEASURING APPARATUS AND METHOD OF A GAS DIFFUSION LAYER FOR FUEL CELLS

CROSS REFERENCE TO RELATED APPLICATION

The present application claims priority of Korean Patent Application Number 10-2014-0038880 filed on Apr. 1, 2014, the entire contents of which application are incorporated herein for all purposes by this reference.

BACKGROUND

1. Technical Field

The present invention relates to an interfacial adhesion strength measuring apparatus and method of a gas diffusion layer for fuel cells, and more particularly, to an interfacial adhesion strength measuring apparatus and method of a gas diffusion layer for fuel cells that quantitatively detect an applied load when fracture or peeling is generated in the gas diffusion layer by adhering the gas diffusion layer to a pair of cantilevers using different adhesives and then applying force to the gas diffusion layer in a direction in which the gas diffusion layer is separated.

2. Description of the Related Art

A stack for a fuel cell vehicle is generally configured of several hundreds of unit cells, each of which includes a membrane electrode assembly (MEA), a gas diffusion layer (GDL), and a separator. Among these components of the unit cell, the gas diffusion layer serves to uniformly supply hydrogen, air, or oxygen, which is reaction gas supplied along channels of a separator, to a surface of the membrane electrode assembly.

In particular, the gas diffusion layer includes a carbon fiber substrate 110 that operates as a support and has a paper form, a cloth form, or a felt form, and a micro porous layer (MPL) 130 present on the substrate 110 in a form in which it is coated, as shown in FIG. 1, wherein the substrate 110 and the micro porous layer 130 have an interface present therebetween. However, in many gas diffusion layers, an interphase region is formed in a shape in which carbon pastes having a predetermined viscosity partially penetrate into a surface of the porous substrate 110 when the micro porous layer is coated, rather than forming a clear interface. A thickness of the interphase region varies depending on a structure of the substrate 110 and a feature of a material of the micro porous layer 130. In addition, the interfaces are structurally more fragile particularly under harsh fuel cell operating conditions. For example, when the stack repeatedly experiences a dry/wet or freeze/thaw cycle environment, a problem such as fracture, peeling, or the like, is first generated on the interface, which has a substantial influence on durability of the fuel cell stack. In other words, interfacial adhesion has been recognized as an important factor capable of determining a lifespan of a fuel cell vehicle.

Generally, as a method of measuring the interfacial adhesion, a scotch tape test method, a scratch test method, and the like, which are indirect and qualitative methods, and a pull-off test method, a peel test method, and the like, which are direct and quantitative methods have been developed. The scotch tape test method is a method of evaluating the adhesion by attaching an adhesive tape having a predetermined length to the surface of the micro porous layer 130 and then detaching the adhesive tape from the surface of the micro porous layer 130. When the micro porous layer 130 is attached to the adhesive tape to be detached from the substrate 110, adhesion between the adhesive tape and the micro porous layer 130 is greater than adhesion between the micro porous layer 130 and the substrate 110. However, this method may determine only whether an examination is passed.

Further, the scratch test method is a method of estimating adhesion by a threshold load value when the micro porous layer 130 is peeled by moving the substrate 110 while increasing a load on the surface of the micro porous layer 130 using a stylus having a round end portion. This method has an advantage that it may be simpler to prepare a sample compared to other methods, such that rapid measurement may be possible, but has a disadvantage that a relationship between a threshold load and actual adhesion of the micro porous layer 130 may not be clearly discovered. The peel test method, which was developed from the scotch tape test method and is devised to quantitatively measure adhesion, is a method of calculating peeling strength by measuring an applied load while detaching a flexible strip having a predetermined width from the firm substrate 110 at a predetermined speed and dividing the measured load with the width of the strip. However, the peel test method may not be applied to a gas diffusion layer in which both of portions that correspond to the strip and the substrate are made of a soft material.

In addition, there is a method of creating a stable crack in the interface between the micro porous layer 130 and the substrate 110 through indentation and then measuring a threshold load required for advancing the crack to calculate adhesion of the micro porous layer 130 based on the fact that the advance of the crack is associated with interface fracture toughness and interfacial adhesion strength. However, in the case of the gas diffusion layer, the crack is not advanced along the interface at the time of the indentation, and both of the substrate 110 and the micro porous layer 130 are damaged. Therefore, this method may not be applied to the gas diffusion layer.

As described above, the existing interfacial adhesion evaluating methods and apparatuses are useful for measuring interfacial adhesion of a thin film coated on a firm and rigid substrate such as a metal, but may not quantitatively evaluate interfacial adhesion of a thin and flexible product such as the gas diffusion layer. In the peel test method or the scratch test method using an adhesive tape it may be difficult to compare qualitative and approximate relative adhesion, and requires improvement in several aspects such as efficiency, a cost, a time, and the like. Therefore, the development of an apparatus capable of quantitatively evaluating interfacial adhesion of a gas diffusion layer, which is one of electricity generating components for a stack, has been required.

The matters described as the related art have been provided only for assisting in the understanding for the background of the present invention and should not be considered as corresponding to the related art known to those skilled in the art.

SUMMARY

An object of the present invention is to provide an interfacial adhesion strength measuring apparatus and method of a gas diffusion layer for a fuel cell that quantitatively and more accurately calculate interfacial adhesion of the gas diffusion layer for a fuel cell using a pair of cantilevers. In addition, the present invention provides an adhesive selecting method and reference capable of being more optimally applied particularly to a structure configured of a soft porous substrate and a dense micro porous layer.

According to an exemplary embodiment of the present invention, an interfacial adhesion strength measuring apparatus of a gas diffusion layer for a fuel cell may include: a pair of load applying parts each adhered to outer surfaces of a substrate configuring the gas diffusion layer of the fuel cell and a micro porous layer coated on the substrate and applying tension force in a direction in which the substrate and the micro porous layer are separated from each other; a first adhering part applied to one of the load applying parts (e.g., a first load applying part) and adhered to the substrate; and a second adhering part applied to the other of the load applying parts (e.g., a second load applying part) and adhered to the micro porous layer, wherein the first and second adhering parts contain materials of which contact angles with the substrate or the micro porous layer are different from each other, respectively.

A contact angle formed between a material contained in the first adhering part and the substrate may be less than a contact angle formed between a material contained in the second adhering part and the micro porous layer. A contact angle formed between a material contained in the first adhering part and the substrate may be about 1 to 55 degrees, and a contact angle formed between a material contained in the second adhering part and the micro porous layer may be about 70 to 170 degrees. A contact angle formed between a material contained in the first adhering part and the substrate and a contact angle formed between a material contained in the second adhering part and the micro porous layer may have a ratio of about 1:x set therebetween. The set 'x' may be any one of values between 1.27 and 170.

The first and second adhering parts may be adhesives that have adhering materials containing different components. The load applying part may include: a pair of cantilevers adhered to the substrate or the micro porous layer; and an operating part applying tension force in a pulling direction to the pair of cantilevers. The first and second adhering parts may be applied in a length direction of the pair of cantilevers.

The operating part may be connected to each of end portions of the pair of cantilevers and may apply tension force to the pair of cantilevers. The operating part may include: a frame that vertically forms supports; a pair of lift bars connected to end portions of the pair of cantilevers, respectively, and extended upwardly or downwardly; a driving part disposed at an upper end of the frame and moving the upwardly extended lift bars upwardly to apply pulling tension force to the pair of cantilevers; and a road cell disposed on a bottom surface of the frame and coupled to the downwardly extended lift bars to detect a magnitude of the tension force applied to the pair of cantilevers while driving the driving part.

According to another exemplary embodiment of the present invention, an interfacial adhesion strength measuring method of a gas diffusion layer for a fuel cell may include: applying first and second adhering parts, respectively, to a pair of cantilevers adhered to outer surfaces of a substrate configuring the gas diffusion layer of the fuel cell and a micro porous layer coated on the substrate; adhering the pair of cantilevers to the outer surfaces of the substrate and the micro porous layer, respectively; and applying tension force to the pair of cantilevers in a direction in which the substrate and the micro porous layer are separated from each other, wherein the first and second adhering parts contain materials of which contact angles with the substrate or the micro porous layer are different from each other, respectively. A contact angle formed between a material contained in the first adhering part and the substrate may be less than a contact angle formed between a material contained in the second adhering part and the micro porous layer.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention, and wherein.

DETAILED DESCRIPTION

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/of" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although exemplary embodiment is described as using a plurality of units to perform the exemplary process, it is understood that the exemplary processes may also be performed by one or plurality of modules. Additionally, it is understood that the term controller refers to a hardware device that includes a memory and a processor. The memory is configured to store the modules and the processor is specifically configured to execute said modules to perform one or more processes which are described further below.

Figure 1:
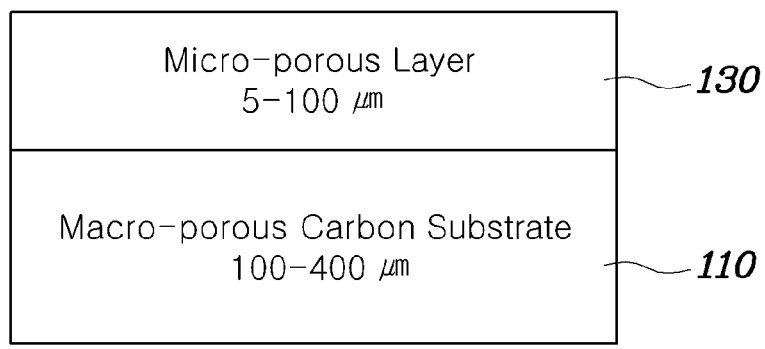
FIG. 1 is an exemplary diagram showing a structure of a gas diffusion layer for a fuel cell according to the related art.
Figure 2:
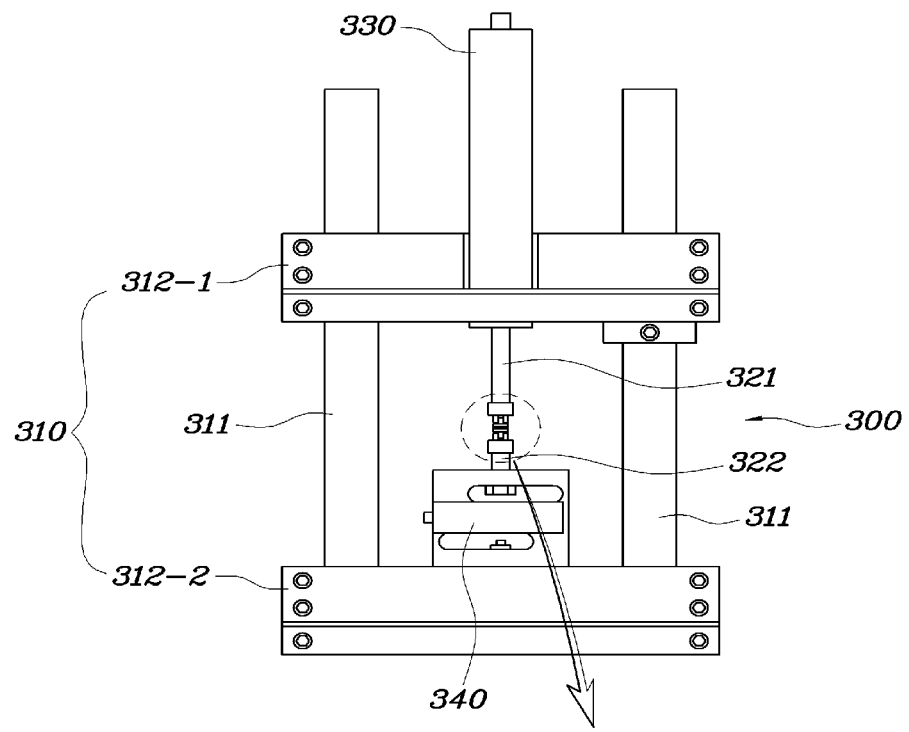
FIG. 2 is an exemplary configuration diagram of an interfacial adhesion strength measuring apparatus of a gas diffusion layer for a fuel cell according to an exemplary embodiment of the present invention.
Figure 2:
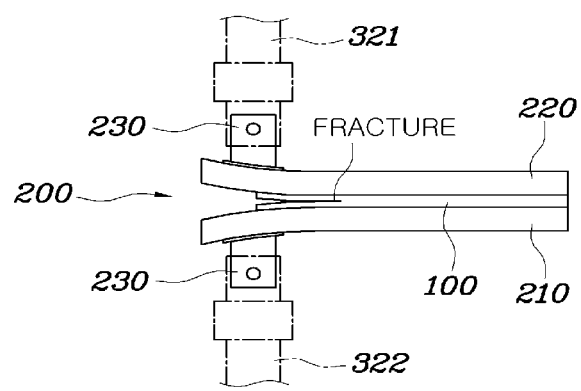
Figure 3:
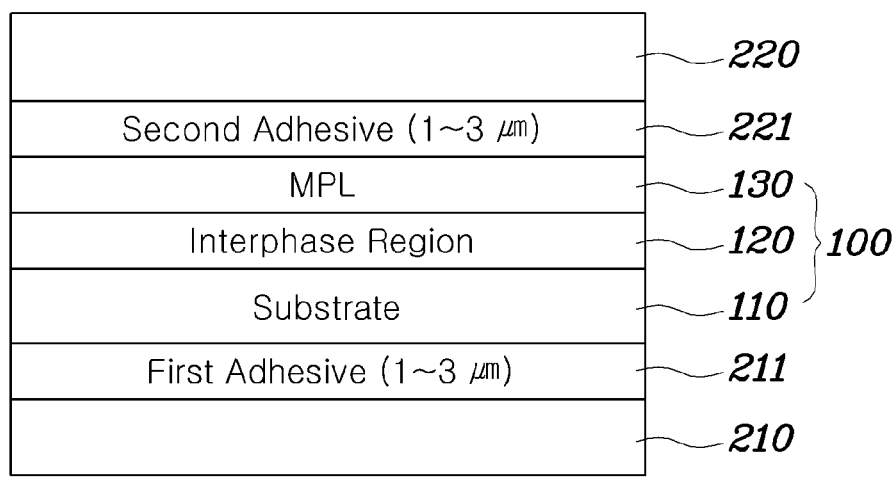
FIG. 3 is an exemplary diagram showing a coupling structure of the gas diffusion layer and a load applying part according to an exemplary embodiment of the present invention.

Hereinafter, an interfacial adhesion strength measuring apparatus and method of a gas diffusion layer for a fuel cell according to an exemplary embodiment of the present invention will be described with reference to the accompanying drawings. FIG. 2 is an exemplary configuration diagram of an interfacial adhesion strength measuring apparatus of a gas diffusion layer for a fuel cell according to an exemplary embodiment of the present invention; and FIG. 3 is an exemplary diagram showing a coupling structure of the gas diffusion layer and a load applying part according to an exemplary embodiment of the present invention.

The interfacial adhesion strength measuring apparatus of a gas diffusion layer for a fuel cell according to an exemplary embodiment of the present invention may include a pair of load applying parts 200 each adhered to outer surfaces of a substrate 110 configuring the gas diffusion layer 100 of the fuel cell and a micro porous layer 130 coated on the substrate 110 and configured to apply tension force in a direction in which the substrate 110 and the micro porous layer 130 are separated from each other; a first adhering part 211 applied to one of the load applying parts (e.g., a first load applying part) 200 and adhered to the substrate 110; and a second adhering part 221 applied to the other of the load applying parts (e.g. a second load applying part) 200 and adhered to the micro porous layer 130, wherein the first and second adhering parts 211 and 221 contain materials of which contact angles with the substrate 110 or the micro porous layer 130 are different from each other, respectively.

Furthermore, the outer surfaces of the substrate 110 and the micro porous layer 130 indicate surfaces on which the substrate 110 and the micro porous layer 130 are not coupled to each other. The first and second adhering parts 211 and 221 will be described in more detail. The first and second adhering parts 211 and 221, which may be configured of adhesives having adhering materials containing different components, serve to generate fracture in an interphase region 120 between the substrate 110 and the micro porous layer 130 when the substrate 110 or the micro porous layer 130 is adhered to the load applying part 200. In addition, the tension force in a pulling direction acts in the load applying part 200 to separate the substrate 110 and the micro porous layer 130 from each other. Although applied thicknesses of the first and second adhering parts 211 and 221 may be set to be different from each other depending on the substrate 110 or the micro porous layer 130, in an exemplary embodiment, the applied thicknesses may be about 1 to 3 μm.

In particular an overlapped interphase region may be formed in a shape in which carbon pastes having a predetermined viscosity partially penetrate into a surface of the porous substrate 110 when the micro porous layer is coated, rather than forming a clear interface between the substrate 110 and the micro porous layer 130. As a thickness of the interphase region 120 increases, coupling force, that is, interfacial adhesion may increase and generation of fracture or peeling in the interphase region 120 may decrease, thus increasing the strength of the gas diffusion layer 100. In other words, since a coupling degree of the interphase region 120 may determine strength of the gas diffusion layer 100, when the tension force of the load applying part 200 is applied, peeling may be generated more accurately in the interphase region 120.

Accordingly, adhesives containing adhering materials having different contact angles may be used on the outer surfaces of the substrate 110 and the micro porous layer 130, respectively since structures and surface characteristics of the substrate 110 and the micro porous layer 130 may be different from each other. In other words, since the micro porous layer 130 may have a form of a substantially thin film having a substantially thin thickness and many cracks may be present in a surface thereof, an adhesive having a substantially low contact angle may permeate more easily into the micro porous layer 130 through the cracks generally formed in the micro porous layer 130. In addition, adhesion of the adhesive may have an influence on the interphase region 120 when the adhesive directly contacts the interphase region 120, such that it may be difficult to accurately measure interfacial adhesion.

Therefore, an adhesive containing a material having a higher contact angle than that of the adhesive used for adhering the substrate 110 may be used in the micro porous layer 130 to prevent the adhesive from permeating into the micro porous layer 130. Further, the substrate 110 may have a structure in which carbon fibers are unevenly entangled, and a thickness greater than that of the micro porous layer 130. In addition, since a surface of the substrate 110 may not be formed as a substantially uniform thin film, when the adhesive does not permeate into the substrate 110, but is applied to the surface of the substrate 110, the load applying part 200 may not be easily adhered to the substrate 110. Therefore, an adhesive containing a material having a lower contact angle than that of the adhesive used for the micro porous layer 130 may be used on the outer surface of the substrate 110.

The contact angle will be further explained. The contact angle, which may be an angle formed between liquid and a surface of an object that the liquid contacts, indicates an angle formed between a tangential line and the surface when the tangential line is drawn from a point at which the liquid contacts the surface of the object to the liquid. When the contact angle is substantially high (e.g., greater than a predetermined contact angle), liquid has substantially strong cohesive force and forms almost to a spherical shape, and when the contact angle is substantially low (e.g., less than a predetermined contact angle), liquid has relatively weak cohesive force and may be widely spread in a semi-spherical or oval form. Therefore, liquid having a relatively high contact angle may not easily permeate into the object, and liquid having a substantially low contact angle may permeate more easily into the object. Since a method of measuring the contact angle is the same as a method generally used in the related art, a detailed description thereof will be omitted.

Therefore, the materials used in the first and second adhering parts 211 and 221 in an exemplary embodiment of the present invention may be adhering materials having different contact angles, and the adhering materials may be selected with a contact angle formed between the adhering material contained in the first adhering part 211 and the substrate 110 that less than a contact angle formed between the adhering material contained in the second adhering part 221 and the micro porous layer 130. Therefore, adhesives containing several adhering materials, for example, epoxy based and acryl based materials separately drop on the same sample as those of the substrate 110 and the micro porous layer 130 to measure contact angles, and measured values may be stored as data, thereby making it possible to select appropriate materials allowing the substrate 110 and the micro porous layer 130 to be maintained in a state in which they may be adhered to the pair of load applying parts, respectively, while allowing peeling to be generated in the interphase region 120 while performing an interfacial adhesion measurement experiment of the interphase region 120.

The following Table 1 shows measured interfacial adhesion based on a content of polytetrafluoroethylene (PTFE), which is a fluorine based polymer in the substrate 110 of the gas diffusion layer 100.

TABLE 1

| | PTFE [wt. %] in substrate | Kind of adhesive (substrate layer:micro porous layer) | Adhesive contact angle [°] (substrate layer:micro porous layer) | Average interfacial adhesion strength [J/m2] |
|---|---|---|---|---|
| Comparative Example | — | 5 | E-1:E-1 | 46:38 | N/A |
| Inventive Example | A | 0 | E-1:E-2 | 43:85 | 15.7 |
| | B | 10 | E-1:E-2 | 41:87 | 35.2 |
| | C | 20 | E-1:E-2 | 54:77 | 52.6 |

In particular, the same E-1 adhesive is used in both of the first and second adhering parts 211 and 221 in Comparative Example, while E-1 is an adhering material used in the first adhering part 211 and E-2 is an adhering material used in the second adhering part 221 in Inventive Example.

The PTFE will be described prior to a description of Table 1. Since a fuel cell system has a reaction mechanism in which water may be produced, when the produced water is present in the substrate 110 of the gas diffusion layer, a reaction gas may not be smoothly diffused, such that electrochemical performance may deteriorate. Therefore, the substrate 110 is generally subjected to water repellent treatment to remove the water in the gas diffusion layer. To increase water repellency, the PTFE, which is a hydrophobic fluorine based polymer, may often be used. In particular, a physical property of the interface between the substrate 110 and the micro porous layer 130 may change based on a content of the fluorine based polymer in the substrate 110. In addition, based on whether the PTFE is present and based on a degree of the contained PTFE, a portion of the micro porous layer 130 may be impregnated into the substrate 110 to form the interphase region 120 or adjust a thickness of the interphase region 120, such that fracture paths may be different from each other.

Figure 4:
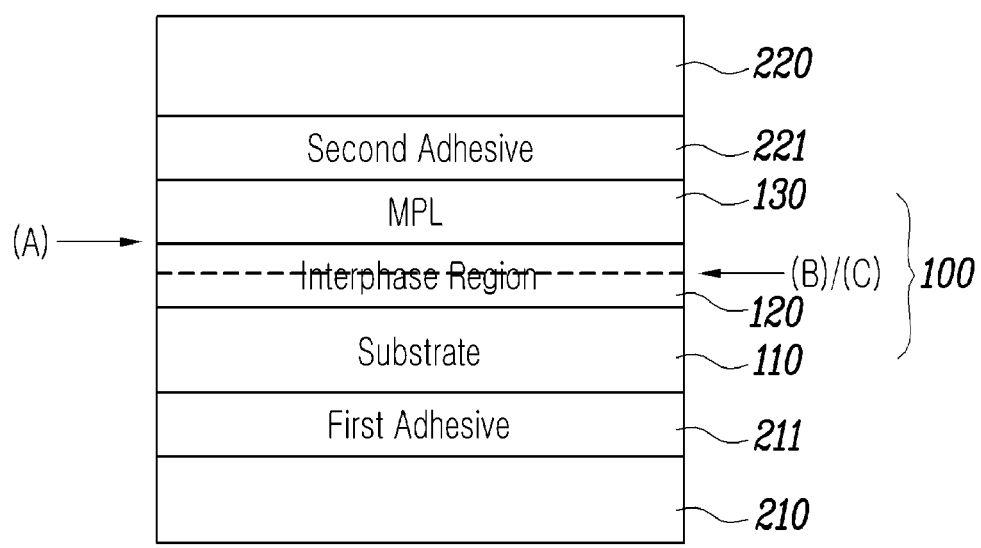
FIG. 4 is an exemplary diagram showing a fracture position of the gas diffusion layer according to an exemplary embodiment of the present invention.

Comparative Example in Table 1 corresponds to when the same epoxy based adhering material is used in the substrate 110 and the micro porous layer 130. In particular, Table 1 shows that fracture is not generated in the interphase region 120, but is generated between the micro porous layer 130 and the interphase region 120, as shown in FIG. 4. According to multiple experiments, in the case of the Comparative Example, a fracture path was undulated while moving to and from the substrate 110 and the micro porous layer 130. In other words, reliable interfacial adhesion may not be obtained. Additionally, contact angles formed between the adhesives and surfaces of the substrate 110 and the micro porous layer 130 were 46 degrees and 38 degrees, which are substantially similar to each other. The adhering material used in the second adhering part 221 has passed through the micro porous layer 130 and has then permeated into the substrate 110, such that the interphase region 120 is affected by the adhering material. Therefore, an irregular fracture shape has appeared.

Moreover, as shown in Inventive Example, when different adhesives are applied on the surfaces of the substrate 110 and the micro porous layer 130, normal fracture has progressed in the interphase region 120, and quantitative interfacial adhesion strength might be obtained. In particular, a contact angle formed between the adhering material used in the first adhering part 211 and the surface of the substrate 110 was present between 41 to 54 degrees, and a contact angle formed between the adhering material used in the second adhering part 221 and the surface of the micro porous layer 130 was present between 76 to 87 degrees.

In addition, a correlation between a content of the PTFE and the interfacial adhesion may also be recognized. As a result, as the content of the PTFE is increased, the interfacial adhesion was increased, and interfacial fracture paths were different from each other based on whether the PTFE is present, as shown in FIG. 4. In other words, in the case of (A) in which the PTFE is not present in the substrate 110, the interphase region 120 is not present, such that the substrate 110 and the micro porous layer 130 were fractured, while in the case of (B) and (C) in which the PTFE is present in the substrate 110, fracture was generated in the interphase region 120. The reason why the interfacial adhesion is increased as the content of the PTFE is increased is that a thickness of the interphase region 120, that is, a portion at which the micro porous layer 130 is overlapped with the substrate 110 was increased or coupling force between the PTFE present in the substrate 110 and the PTFE present in the micro porous layer 130 was increased.

As seen in the above Table 1, when types of the adhering materials used in the substrate 110 and the micro porous layer 130 are different from each other, the fracture may be induced to be generated in the interphase region 120. Therefore, the interfacial adhesion may be quantitatively measured. Particularly, when the contact angle formed between the adhering material contained in the first adhering part 211 and the substrate is about 1 to 55 degrees and the contact angle formed between the adhering material contained in the second adhering part 221 and the micro porous layer is about 70 to 170 degrees, the adhering materials may be maintained in a state in which they may be adhered to the pair of load applying parts 200 without having an influence on the interphase region 120. It may be appreciated through the fact that the adhering material permeates into the interphase region 120, such that a fractured portion may become unstable when the contact angle of the adhering material used in the micro porous layer 130 in Comparative Example of the above Table 1 is less than 70 degrees.

Furthermore, the contact angle formed between the adhering material contained in the first adhering part 211 and the substrate 110 and the contact angle formed between the adhering material contained in the second adhering part 221 and the micro porous layer 130 may have a ratio of about 1:x set therebetween, wherein x may be a contact angle difference value between used adhering components based on characteristics of the substrate 110 and the micro porous layer 130 and may be any one of values between about 1.27 and 170. The ratio may be set to allow a minimum difference to be generated between the contact angle formed between the adhering material contained in the first adhering part 211 and the substrate 110 and the contact angle formed between the adhering material contained in the second adhering part 221 and the micro porous layer 130, thereby making it possible to induce the fracture to be generated accurately in the interphase region 120.

Next, an operation structure of the interfacial adhesion strength measuring apparatus of a gas diffusion layer for a fuel cell according to an exemplary embodiment of the present invention will be described. The load applying part 200 may include a pair of cantilevers 210 and 220 adhered to the substrate 110 or the micro porous layer 130 and an operating part 300 configured to apply tension force in a pulling direction to the pair of cantilevers 210 and 220.

The operating part 300 may include a frame 310 that vertically forms supports; a pair of operating bars 321 and 322 connected to end portions of the pair of cantilevers 210 and 220, respectively, and extended upwardly or downwardly; a driving part 330 disposed at an upper end of the frame 310 and configured to move the upwardly extended operating bars 321 and 322 upwardly to apply tension force to the pair of cantilevers 210 and 220; and a road cell 340 disposed on a bottom surface of the frame 310 and coupled to the downwardly extended operating bars 321 and 322 to detect a magnitude of the tension force applied to the pair of cantilevers 210 and 220 at the time of driving the driving part 330. In particular, the pair of cantilevers 210 and 220 may be disposed horizontally in parallel with the gas diffusion layer 100 in a length direction and may be disposed to face each other in a vertical direction. In addition, the pair of cantilevers 210 and 220 may include an upper cantilever 220 and a lower cantilever 210. Thicknesses of the respective cantilevers may be variously set and in an exemplary embodiment the thicknesses may be about 3 mm.

The frame 310 may include a plurality of vertical bars 311 that vertically form the supports and a plurality of horizontal bars 312-1 and 312-2 that connect the respective vertical bars 311 to each other at upper and lower ends of the vertical bars 311. The pair of operating bars 321 and 322 may include an upper lift bar 321 having one end (e.g., a first end) connected to the end portion of the upper cantilever 220 and the other end (e.g., a second end) connected to the driving part 330 and a lower fixed bar 322 having one end (e.g., a first end) connected to the end portion of the lower cantilever 210 and the other end (e.g., a second end) connected to the road cell 340. Various coupling structures such as hooking structure, a bolting structure, or the like, may be used to connect between the respective components, and the upper and lower cantilevers 220 and 210 may include a plurality of protrusions 230 provided thereabove and therebelow, respectively, and apertures are formed in the protrusions 230, respectively, to couple the upper and lower cantilevers 220 and 210 to an end of the upper lift bar 321 and the lower fixed bar 322 by pins, respectively.

In addition, the driving part 330 may be driven by a hydraulic cylinder or a motor, may be fixed to the upper horizontal bar 312-1 that connects the upper ends of the plurality of vertical bars 311 to each other, and may be coupled to the upper lift bar 321 to allow the upper lift bar 321 to be moved vertically. The driving part 330 is not limited to being driven by the hydraulic cylinder or the motor and may be driven by any other mechanism.

Through the configuration as described above, when the upper lift bar 321 is moved upwardly, the tension force may be applied to upper and lower portions of the pair of cantilevers 210 and 220. In particular, the road cell 340 may be configured to detect a magnitude of the pulling force and store or output the detected magnitude in a controller (not shown) or to a display device. Therefore, a magnitude of force of an instant at which the substrate 110 and the micro porous layer 130 are fractured may be recognized. Further, the lower horizontal bar 312-2 that connects the lower ends of the vertical bars 311 to each other may be configured to support the vertical bars 311 and an upper surface of the lower horizontal bar 312-2 may become the bottom surface of the frame 310.

Although the case in which the road cell 340 is disposed on the lower horizontal bar 312-2 and the driving part 330 is disposed on the upper horizontal bar 312-1 has been described in the present exemplary embodiment, the driving part 330 may be disposed on the lower horizontal bar 312-2 and the road cell 340 may be disposed on the upper horizontal bar 312-1 in another exemplary embodiment. Further, the first and second adhering parts 211 and 221 may be applied in a length direction of the pair of cantilevers 210 and 220 since force may act vertically to the length direction of the pair of cantilevers 210 and 220. In addition, interfacial adhesion may thus be measured between the substrate 110 and the micro porous layer 130.

Figure 5:
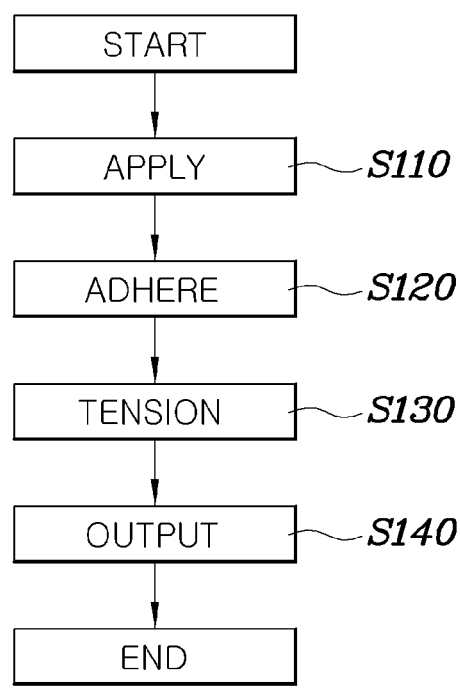
FIG. 5 is an exemplary flow chart of an interfacial adhesion strength measuring method of a gas diffusion layer for a fuel cell according to an exemplary embodiment of the present invention.

FIG. 5 is an exemplary flow chart of an interfacial adhesion strength measuring method of a gas diffusion layer for a fuel cell according to an exemplary embodiment of the present invention. The interfacial adhesion strength measuring method of a gas diffusion layer for a fuel cell using the configuration of the interfacial adhesion strength measuring apparatus of a gas diffusion layer for a fuel cell may include applying the first and second adhering parts 211 and 221 (S110), respectively, to the pair of cantilevers 210 and 220 adhered to the outer surfaces of the substrate 110 configuring the gas diffusion layer 100 of the fuel cell and the micro porous layer 130 coated on the substrate 110; adhering the pair of cantilevers 210 and 220 to the outer surfaces of the substrate 110 and the micro porous layer 130, respectively (S120); and applying a tension force to the pair of cantilevers 210 and 220 in a direction in which the substrate 110 and the micro porous layer 130 are separated from each other (S130).

In the tensioning step S130, the magnitude of the applied tension force may be measured by the road cell 340, and the measured value may be output through the separately provided controller or display device (S140). In addition, in the applying step S110, the first and second adhering parts 211 and 221 may be applied directly to the substrate 110 and the micro porous layer 130, respectively.

With the interfacial adhesion strength measuring apparatus and method of a gas diffusion layer for a fuel cell having the structure as described above, a problem occurring when using a scotch tape test method according to the related art may be overcome. In particular, a problem that the interface between the substrate layer and the micro porous layer of the gas diffusion layer is not easily separated due to insufficiency of adhesion of a scotch tape may be overcome, and an interfacial crack may be more stably generated, such that it may be possible to quantitatively evaluate the interfacial adhesion. Particularly, the present invention may be applied to various soft samples to which the scratch method, or the like, may not be applied, and may provide quantitative interfacial adhesion data. Further, according to the present invention, a problem that a portion of a sample should be gripped when a peeling test method, or the like, is used may be overcome.

Although the present invention has been shown and described with respect to specific exemplary embodiments, it will be obvious to those skilled in the art that the present invention may be variously modified and altered without departing from the spirit and scope of the present invention as defined by the following claims.

What is claimed is:

1. An apparatus for measuring an interfacial adhesion strength for a fuel cell, the apparatus comprising:

a substrate of a gas diffusion layer;
a microporous layer of the gas diffusion layer;
a first load applying part;
a second load applying part;
a first adhesive material applied to the first load applying part which adheres to an outer surface of the substrate of the gas diffusion layer; and
a second adhesive material applied to the second load applying part which adheres to an outer surface of the micro porous layer of the gas diffusion layer,
wherein the first load applying part and the second load applying part apply tension force in a direction in which the substrate and the micro porous layer are separated from each other, and
wherein a first contact angle which the first adhesive material forms with the substrate is different from a second contact angle which the second adhesive material forms with the micro porous layer.

2. The apparatus of claim 1, wherein the first contact angle is less than the second contact angle.

3. The apparatus of claim 1, wherein the first contact angle is about 1 to 55 degrees, and the second contact angle s about 70 to 170 degrees.

4. The apparatus of claim 1, wherein the first contact angle and the second contact angle have a ratio of 1:x set therebetween.

5. The apparatus of claim 4, wherein the set x is a value between about 1.27 and 170.

6. The apparatus of claim 1, wherein the first and second adhesive materials contain different components from each other.

7. The apparatus of claim 1, wherein
the first load applying part includes a first cantilever adhered to the substrate and the second load applying part includes a second cantilever adhered to the micro porous layer, and
wherein the apparatus further includes an operating part configured to apply tension force in a pulling direction to the first and second cantilevers.

8. The apparatus of claim 7, wherein the first and second adhesive materials are applied in a length direction of the first and second cantilevers.

9. The apparatus of claim 7, wherein the operating part is connected to each end portion of the first and second cantilevers and is configured to apply tension force to the first and second cantilevers.

10. The apparatus of claim 7, wherein the operating part includes:
a frame that vertically forms supports;
a pair of lift bars connected to end portions of the first and second cantilevers, respectively, and extended upwardly or downwardly;
a driving part disposed at an upper end of the frame and configured to move the upwardly extended lift bars upwardly to apply pulling tension force to the first and second cantilevers; and
a road cell disposed on a bottom surface of the frame and coupled to the downwardly extended lift bars to detect a magnitude of the tension force applied to the first and second cantilevers while driving the driving part.

11. A method for measuring an interfacial adhesion strength of a gas diffusion layer for a fuel cell, the method comprising:
applying first and second adhesive materials to first and second cantilevers, respectively;
adhering the first cantilever to an outer surface of a substrate of the gas diffusion layer by the first adhesive material and the second cantilever to an outer surface of a micro porous layer of the gas diffusion layer by the second adhesive material; and
applying a tension force to the first and second cantilevers in a direction in which the substrate and the micro porous layer are separated from each other,
wherein a first contact angle which the first adhesive material forms with the substrate is different from a second contact angle which the second adhesive material forms with the micro porous layer.

12. The method of claim 11, wherein the first contact angle is less than the second contact angle.

* * * * *